United States Patent [19]

Shapiro et al.

[11] Patent Number: 5,027,812
[45] Date of Patent: Jul. 2, 1991

[54] TRACHEAL TUBE FOR LASER SURGERY

[75] Inventors: Seymour W. Shapiro; William A. Depel, both of Lowell, Ind.

[73] Assignee: Bivona, Inc., Gary, Ind.

[21] Appl. No.: 518,315

[22] Filed: May 4, 1990

Related U.S. Application Data

[63] Continuation of Ser. No. 409,272, Sep. 19, 1989, abandoned, which is a continuation of Ser. No. 795,279, Nov. 5, 1985, abandoned.

[51] Int. Cl.$^5$ .............................................. A61M 16/00
[52] U.S. Cl. .................................... 128/207.15; 604/96
[58] Field of Search ....................... 128/200.26, 207.14, 128/207.15, 303.1, 656, 657, 658; 604/93, 96, 280, 282, 283, 106; 138/108, 114, 118, 121, 129, 131, 137, DIG. 7, DIG. 6

[56] References Cited

U.S. PATENT DOCUMENTS

| | | | |
|---|---|---|---|
| 3,554,484 | 12/1974 | Jackson | 128/207.15 |
| 3,640,282 | 2/1972 | Kamen et al. | 128/207.15 |
| 3,799,173 | 3/1974 | Kamen | 128/207.15 |
| 4,063,561 | 12/1977 | McKenna | 128/207.15 |
| 4,378,796 | 4/1983 | Milnaud | 128/207.15 |
| 4,411,655 | 10/1983 | Schreck | 604/281 |
| 4,489,722 | 12/1984 | Ferraro et al. | 128/207.15 |
| 4,495,948 | 1/1985 | Shapiro | 128/207.15 |
| 4,550,558 | 4/1986 | Cabrera et al. | 128/303.1 |
| 4,558,093 | 12/1985 | Hatzenbuhler et al. | 125/303.1 |
| 4,607,635 | 8/1986 | Heyden | 128/207.15 |
| 4,632,108 | 12/1986 | Geil | 128/207.15 |
| 4,649,915 | 3/1987 | Heyden | 604/100 |

FOREIGN PATENT DOCUMENTS

| | | | |
|---|---|---|---|
| 609038 | 10/1932 | Fed. Rep. of Germany | 128/207.15 |
| 406252 | 12/1909 | France | 138/131 |
| 2463624 | 4/1981 | France | 128/209.15 |

OTHER PUBLICATIONS

LeJeune, Jr. et al., "Heat Sink Protection For Endotrachal Cuffs-$CO_2$Laser", Presented to American Bronchio Esophagologicl Association, May 4, 1982 Palm Beach, Florida.

Ohio Chemical, "Endotracheal Tube Adapters", Anesthesia Apparatus and Accessories Catalog, Jul. 20, 1966, pp. 44-45.

Primary Examiner—Randell L. Green
Assistant Examiner—K. M. Reichle
Attorney, Agent, or Firm—Emrich & Dithmar

[57] ABSTRACT

A cuffed tracheal tube for use in intubation of a trachea of a patient during laser surgery involving the head or neck of the patient, includes a flexible aluminum conduit, and an expandable cuff carried at one end of the conduit and including a body of sponge-like material enclosed within a cover filled with water which saturates the sponge-like body while expanding the cuff to provide a seal between the tracheal tube and the trachea of the patient. The flexible aluminum conduit and the water saturated cuff define a heat dispersion medium for absorbing laser energy engaging the tracheal tube.

11 Claims, 1 Drawing Sheet

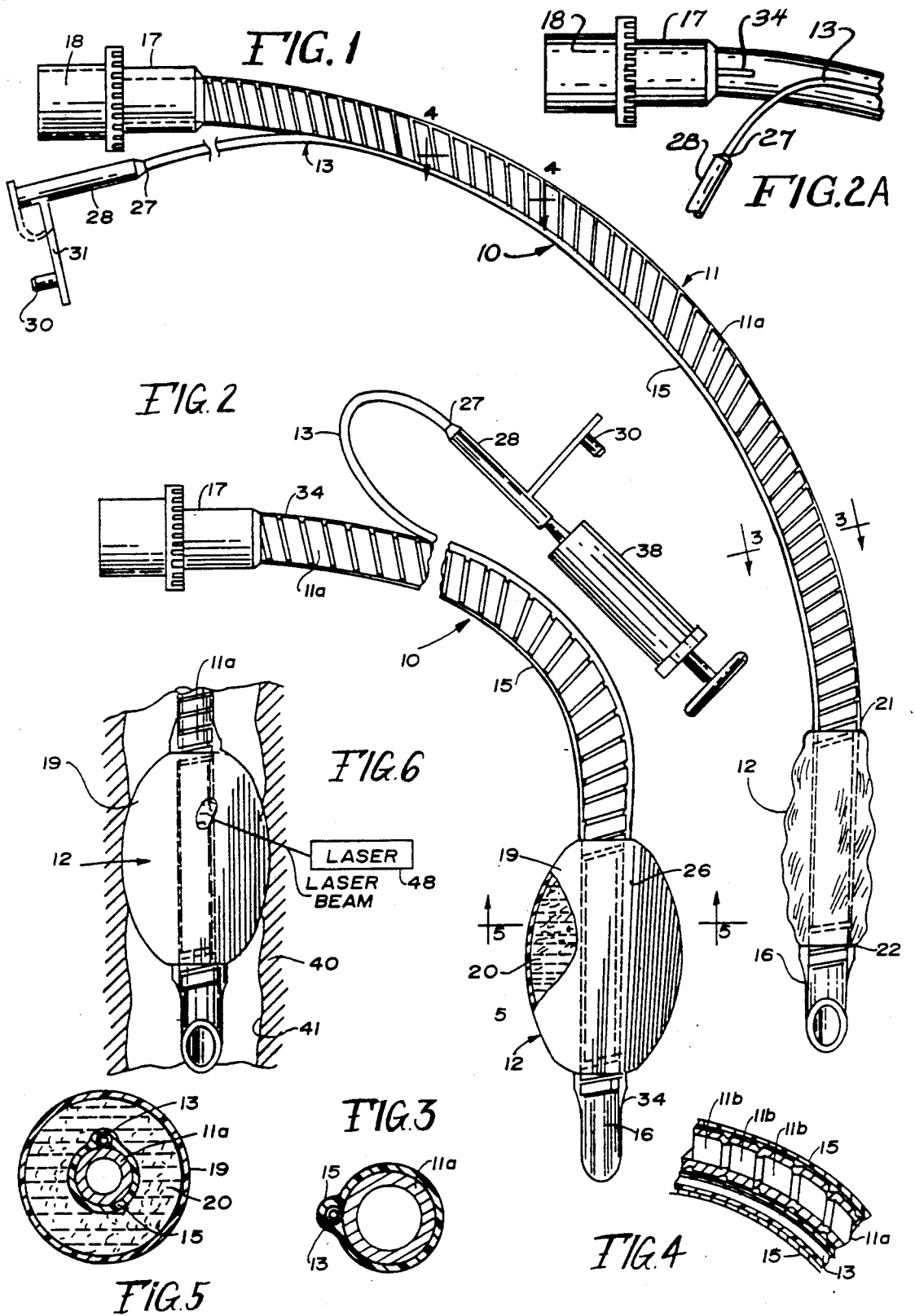

TRACHEAL TUBE FOR LASER SURGERY

This is a continuation of application Ser. No. 07/409,272, filed Sept. 19, 1989, which is now abandoned; that application is a continuation of application Ser. No. 795,279, filed Nov. 5, 1985, which is now abandoned.

BACKGROUNF OF THE INVENTION

The present invention relates to tracheal tubes and, more particularly, to tracheal tubes for use in laser surgery.

As is well known in the art, tracheal tubes are commonly inserted into a person's trachea for various purposes. One such purpose is to provide a means for administering a general anesthetic. Such tubes usually are provided with a tracheal cuff to insure a tracheal seal, both to prevent loss of administered gas and to prevent aspiration of body fluids. Thus, tracheal tubes commonly in use, are provided with a cuff at one end of the tube, which is expandable outwardly into engagement with the inner wall of the trachea. Cuffed tracheal tubes as known in the art, include those having cuffs or balloons made of latex rubber, plastic, silicone, etc. The cuff is mounted on the main tube and is usually attached to surround the tube in communication with an inflation line. When being inserted into the trachea, the cuff is in uninflated or, deflated condition. After the intubation device has been inserted into the trachea, the cuff is inflated like a balloon, by feeding air into the cuff to expand the cuff into engagement with the inner wall of the trachea to provide a seal thereagainst.

Another type of cuffed tracheal tube embodies a cover filled with resilient material, with the cuff normally being disposed in expanded position and being collapsed by applying a vacuum thereto during insertion or removal of the tube into or from the trachea, respectively.

The progress of laser technology has resulted in increased use of laser beams in surgical operations. Laser beams are characterized by high energy and power densities. Because laser beams are light rays, they can be focused very precisely allowing them to be used for various types of surgery. Light from a laser is focused by a lens system to a small spot of light of great intensity, producing strong heating, allowing vaporization of a small amount of virtually any substance, at locations within the body with minimal surgical invasiveness. These factors permit laser surgery to be highly advantageous in many situations in comparison to conventional surgical techniques.

In the case of surgery involving the head or neck area of the body, the laser beam may be directed in the proximity of the trachea tube. Conventional trachea tubes are made of plastic, latex or rubber materials and, as such, when used during laser surgery involving the head or neck portion of a patient, such tubes are likely to be ignited by the high intensity laser beam striking the tube resulting in the generation of heat, flame and toxic fumes within the patient's trachea. Because anesthetic gases are administered together with oxygen in high concentration under positive pressure, conventional tracheal tubes are not safe for use during laser surgery of the head and neck. Tracheal tube ignition may result not only in burning of the patient's tracheal and bronchial tree, but also may result in the inhalation of toxic fumes resulting from such burning. To overcome such problems, it has been common practice to wrap the tube portion of the tracheal tube with an aluminum foil or tape to shield the tube from the laser beam. However, because the cuff portion of the tube must be capable of expansion, it is impractical to wrap the cuff in aluminum foil or tape. Thus the cuff portion, which provides the requisite seal between the tracheal tube and the trachea, remains vulnerable to damage by the laser beam. Although striking an air filled cuff with a laser beam is less likely to result in a fire, it will result in cuff deflation. The resulting loss of the tracheal seal often requires removal of the tracheal tube and replacement with an intact unit. A similar situation results when the laser beam penetrates the air inflation line to the cuff. A limited degree of protection for the cuff has been achieved by placing cotton soaked in saline or water around the cuff after insertion of the cuff and expansion of the tube to maintain a moist surface about the expanded cuff. However, this approach has not proven entirely satisfactory.

Another attempt at providing a tracheal tube for use during laser surgery involves the use of a laminated silicone tube having an outer coating impregnated with aluminum flakes. However, such a structure offers only limited protection. Additionally, such a structure utilizes an air inflated cuff to provide the requisite seal. Although this approach provides a degree of protection from the laser beam, such tubes are known to have ignited. Further, should the cuff be penetrated by the laser beam, the cuff deflates and the seal between the tracheal tube and the patient's trachea is lost. An uncuffed metal tube commonly referred to as the Norton tube, is available for use during laser surgery, however, the Norton tube has not proven to be satisfactory since it lacks a cuff and has limited flexibility, limiting its capability to conform to the patient's airway.

SUMMARY OF THE INVENTION

It is the object of the present invention to provide an improved tracheal tube.

Another object of the invention is to provide a tracheal tube assembly for use in head and neck surgery and which is safe for use during laser surgery of the head and neck, by providing a flexible metal tube interior to serve as a heat dispenser or heat sink for dispersion of the laser energy.

Yet another object of the invention is to provide a cuffed tracheal tube assembly which maintains its seal between the trachea and the tracheal tube in the event the cuff or the cuff inflation line is penetrated by a laser beam.

A further object of the invention is to provide a cuffed tracheal tube assembly including a cuff portion which provides a heat barrier or heat dispersion medium for absorbing laser energy.

These and other objects are achieved by the present invention which provides a tracheal tube assembly for use in intubation of the trachea of a patient during laser surgery involving the head or neck of the patient, its tracheal tube assembly comprising a tube having a flexible metal conduit shielded by a silicone sheath or coating, with the tube having a proximal end and a distal end, and an expandable cuff carried by said tube near the distal end thereof. The tube includes an inflation line operative connected to the cuff for contracting and expanding the cuff. The cuff is adapted for establishing a seal between the tube and the trachea of the patient. The cuff includes a body portion of sponge-like material, and a cover with the body being enclosed within the cover. The cuff is filled with a liquid through the inflation line which saturates the body portion of the cuff while expanding the cuff and cover into engagement with the inner wall of the trachea of the patient to form a seal between the tube and the tracheal wall. The liquid saturated cuff provides a heat barrier or heat sink or dispersion medium for absorbing the laser energy engaging the cuff.

The present invention consists of certain novel features and a combination of parts hereinafter fully described illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment, from an inspection of which, when considered in connection with the following description, the invention, its construction and operation, and many of its advantages should be readily understood and appreciated.

FIG. 1 is a side sectional view of a cuffed tracheal tube assembly embodying the principles of the present invention, and showing the cuff disposed in its collapsed condition;

FIG. 2 is a fragmentary, side elevational view of the tracheal tube assembly shown in FIG. 1 illustrating the cuff in the expanded position or sealing condition and with a water or saline filled syringe illustrated for expanding the cuff to the sealing position;

FIG. 2A is a fragmentary top plan view of the proximal end of the tube assembly;

FIG. 3 is a sectional view taken along line 3—3 of FIG. 1;

FIG. 4 is a sectional view taken along line 4—4 of FIG. 1;

FIG. 5 is a sectional view taken along line 5—5 of FIG. 2; and

FIG. 6 is a fragmentary elevational view of the tracheal tube assembly shown in FIG. 2, showing the cuff disposed in sealing engagement with a trachea, shown diagrammatically.

DESCRIPTION OF A PREFERRED EMBODIMENT

Referring to FIG. 1 of the drawings, the tracheal tube assembly 10 provided by the present invention embodies an elongated tube 11 having an inflatable cuff 12, mounted on one end portion thereof, with an inflation line 13 communicating with and extending into the cuff to facilitate deflation and inflation of the cuff, as will hereinafter be described in greater detail. The tracheal tube assembly 10 may be of any suitable construction and is for the purpose of feeding oxygen or the like, into and out of the respiratory tract of a patient during surgery, and in particular during laser surgery involving the head or neck of the patient.

The use of lasers as a means of performing surgery within the body is increasing dramatically. One type of laser is based upon carbon dioxide, has wide range of uses for surgery because it is selectively absorbed by water, a component of all tissue, and because it makes incisions with minimial damage to surrounding tissue. When the tracheal tube assembly 10 is used as an endotracheal tube assembly, the elongated tube 11 is comprised of flexible metal conduit 11A shielded or enclosed within a silicone sheath 15. The metal conduit 11A is of a flexible metal preferably aluminum, or other metal, metal alloy, etc. having a density corresponding to that of aluminum or a density less than that of aluminum.

The tube assembly 10 has a distal end 16 for insertion into the trachea of a patient, and a proximal end 17 on which a connector 18 is mounted for connecting the tracheal tube assembly 10 to a suitable source of anesthetic gas, oxygen, or the like, or, when mechanical ventilation of a respiratory tract is to be carried out, to a ventilating machine, or the like. The tube assembly 10 may be of any suitable length, such tubes commonly being in the nature of nine to fourteen inches in length, when used as an endotracheal tube. The flexible metal conduit 11A is enclosed within the silicone sheath 15 and movable relative to the sheath 15 upon flexure of the conduit 11A.

Referring now to FIGS. 1 and 2, the cuff portion 12 includes a water impervious cover 19 and a cuff body 20 disposed within the cover 19. Both the cuff body 20 and the cuff cover 19 are disposed around a portion of the tube assembly 10 in spaced relation to the ends 16 and 17 thereof. In practice, the cuff portion 12 is normally disposed substantially closer to the end 16 of the tube assembly 10 than to the end 17 thereof, such as, for example, being spaced from the end 16 a distance in the nature of one-half to three-fourths of an inch on a tube having an overall length of fourteen inches. However, the cuff portion 12 may be disposed at any suitable location along the tube assembly 10, the particular location thereof depending upon the intended use of the tracheal tube assembly 10. For example, normally, when end 16 of the tube assembly 10 is to be inserted into the windpipe or trachea only, the cuff portion 12 preferably will normally be spaced a relatively short distance from the distal end 16, such as, for example, the aforementioned one-half to three-fourths of an inch. However, if the tube assembly 10 is to be inserted further than into the trachea, such as, for example, into the bronchia, the cuff portion 12 preferably would be spaced a greater distance from the distal end 16 so that it would remain in the trachea when the distal end 16 was inserted into the bronchia.

The cuff cover 19 is flexible and may be made of any suitable material such as, for example, latex rubber, suitable plastic sheet material, such as, polyvinylchloride, or the like, or silicone rubber. The cover 19 is generally tubular in form, and the end portions 21 and 22 thereof are hermetically sealed to the outer surface of the sheath encased tube 11 by suitable means, such as, for example, being vulcanized thereto or by a suitable cement such as rubber cement, or the like. It is apparent that the body 20 of the cuff portion 12 could be mounted on the conduit 11A and this assembly could be encased within a silicone sheath, rather than the conduit 11A being separately encased within the silicone sheath 15, with the cuff 12 being hermetically sealed thereto.

The cuff body 20 affords a resilient mass which fills the cuff cover 19 between the end portions 21 and 22 thereof and, when the tracheal tube assembly 10 is disposed in normal inoperative position outside the trachea, and is effective to yieldingly hold the cover 19 in the expanded position. The cuff body 20 is made of a sponge-like resilient material having a multitude of open cells or interstices spread therethrough, such as, for example, sponge rubber or a suitable resilient plastic material, such as, for example, foamed polyurethane, or the like.

As shown in the drawings, an inflation line 13 extends along the tube 11 and is encased within the sheath 15 and operatively connected to the cuff portion 12 for operative contracting and expanding of the cuff portion. Inflation line 13 has one end 26 communicating with the cuff portion 12 and a free end 27 which projects outwardly from the sheath 15 at the proximal end 17 of the tube assembly 10. End 27 of the line 13 defines a cylindrical end member 28 defining an inlet port for the inflation line 13. A cylindrical plug 30 is carried by a flexible strap 31 and adapted for insertion into the end of the cylindrical member 28 to seal the port.

Referring to FIGS. 1, 2, 4 and 5, the inflation line 13 extends through the end portion 21 of the cuff cover 19 and is hermetically sealed thereto by the hermetic seal which connects the cover 19 to the tube 11. With this construction, it will be seen that when the inflation line 13 is open to the atmosphere at the end portion 27 thereof, and the tracheal tube assembly 10 is disposed outside of a trachea, the cuff body 20 is effective to yieldingly hold the cuff cover 19 in the outwardly expanded position. To facilitate insertion of the tracheal tube assembly 10 into the trachea of a patient, a vacuum is provided at the free end portion 27 of the inflation line 13, as by use of a syringe 38 or other means. In this way, air or fluid may be withdrawn from within the cuff cover 19 through the inflation line 13 to thereby afford a partial vacuum within the cuff 12 to cause it to collapse to the position as shown in FIG. 1. The withdrawal of air or fluid from within the cuff cover 19 is substantially uniform throughout the entire area between the end portions 21 and 22 thereof so as to effect a relatively uniform substantially complete collapse of all portions of the cuff cover.

An index line 34 (FIG. 2A) may be provided on the silicone sheath 15 on the side of the sheath where the inflation line 13 is located to aid the medical personnel during insertion of the tracheal tube assembly 10 in locating the inflation tube 13 diametrically opposed to the point where the laser surgery is to be performed. This minimizes the chance that the laser beam could be directed to impinge the inflation line 13.

The plug 30 is of such size that it may be manually inserted into and removed from the member 28 on line 13. With this construction, after a partial vacuum has been applied to the cuff portion 12 to thereby move it into a collapsed position, such as shown in FIG. 1, the plug 30 may be manually inserted into the member 28 to thereby close the end 27 of the tube 13 and thereby retain the vacuum in the cuff 12 during manipulation of the tracheal tube assembly 10.

Referring now to FIGS. 2 and 6, to expand the cuff portion 12 to provide the requisite seal between the tracheal tube assembly 10 and the trachea 40 of the patient, a liquid is injected into the interior of the cuff portion 12 through the inflation line 13 using a syringe 38 shown in FIG. 2, the tip of which is inserted into the open end 27 of the inflation line 13 before allowing the cuff to expand. To accomplish this, the plug 30 is removed from the member 28 while the member is held in a collapsed state. The liquid filled syringe is attached to the member 28 and the liquid is injected. The liquid, for example, may be water or a saline solution. The liquid saturates the cuff body 20 of the cuff portion 12 and expands the cuff body 20 to its expanded position to expand the cuff portion 12 to its full expanded position, as shown in FIG. 6, wherein the cuff portion 12 engages the inner wall 41 of the patient's trachea 40. Once expanded, the plug 30 may be reinserted into the member 28 to retain the liquid within the cuff portion 12.

As indicated, the tracheal tube assembly 10 is particularly suited for use in laser surgery involving the neck or throat of a patient. In such an application, the laser beam generated by a laser, represented by block 48 in FIG. 6, may be directed in the proximity of the tracheal tube assembly 10 which is located in the trachea of the patient. The tube 11, which is comprised of an aluminum metal conduit 11A and silicone sheath 15 is impervious to a laser beam generated by surgical carbon dioxide lasers. That is, when a laser beam impinges the tube assembly 10, the aluminum metal conduit 11A will disperse the energy of the laser beam, thereby preventing the laser beam from penetrating through the tube assembly 10 and preventing a flame situation to occur within the tube with its attendant generation of toxic fumes. Moreover, if the laser beam impinges the cuff portion 12, and penetrates the outer covering 19, cuff body 20 may be penetrated as shown in FIG. 6, a seal will be maintained between the cuff portion 12 and the patient's trachea. A seal will be maintained even if inflation line 13 is penetrated. The water or saline saturated cuff portion 12 disperses the energy of the laser and prevents a flame or ignition situation from occurring with its attendant generation of toxic fumes.

It is believed that either the water or saline solution in the space between the cuff cover 19 and the cuff body 20 or the water or saline solution in contact with the cover throughout the cuff body 20 provides a degree of protection for the cuff body from the laser because the liquid absorbs the energy thereof and acts as a heat sink material. This results in a dispersion of the heat within the cuff portion 12 thereby preventing a flame or ignition situation of the cuff body 12 even though the cuff cover 19 may be penetrated by the laser beam. In a similar manner, the flexible aluminum conduit 11A, as shown in FIG. 4, is comprised of ring segments 11B flexibly joined together which provide flexibility to the conduit, disperses heat resulting from the laser beam impinging on the tube assembly 10 during laser surgery. The heat transfer characteristics of the aluminum conduit 11A enables it to effectively resist penetration by the laser beam.

In addition, it will be seen that the present invention affords a novel and practical tracheal tube assembly which is particularly well adapted for use in laser surgery and which is laser proof in that the tracheal tube assembly absorbs energy generated by a surgical laser sufficiently as to preclude flaming of the tube or cuff, and the cuff construction is such as to enable a seal between trachea and tube assembly to be maintained even should the cuff be penetrated by a laser beam.

We claim:
1. A tracheal tube assembly for use in intubation of the trachea of a patient during laser surgery involving the head or neck of the patient, said assembly comprising: a flexible metal conduit having a first end and a second end;

a silicone sheath having a first end, a second end and an outer surface, said metal conduit being enclosed within said silicone sheath with said first end of said sheath disposed adjacent to said first end of said conduit and said second end of said sheath adjacent to said second end of said conduit;

an expandable cuff on said sheath enclosed conduit near the first end of the conduit, said cuff including a body portion of sponge-like material and a tubular cover having first and second ends, said cover enclosing said body portion and having its ends secured to said outer surface of said sheath, an inflation line operatively connected to said cuff, said inflation line having a fluid inlet for communicating the interior of said cuff with a source of a vacuum for collapsing said cuff to a collapsed condition to facilitate insertion of the tube assembly into the patient's trachea, and thereafter communicating the interior of said cuff with a source of liquid for delivering liquid from the source of liquid to said cuff for filling said cuff with liquid from the source of liquid to saturate said body portion of said cuff with the liquid and to expand said cuff from the collapsed condition to an expanded condition into engagement with the inner wall of the trachea of the patient to form a seal between said cuff of the tube assembly and the inner wall of the trachea of the patient, the liquid saturated body portion of said cuff defining a heat dispersion medium for absorbing laser energy impinging on said cuff and maintaining a seal between said cuff and the inner wall of the trachea of the patient in the event the cover is penetrated by the laser beam.

2. An assembly according to claim 1, wherein said fluid inlet of said inflation line is adapted for communication with a source of water.

3. An assembly according to claim 1, wherein said inflation line has a proximal end and a distal end, said distal end of said inflation line extending into said cuff in fluid communication with the interior thereof, and connector means including a connector body mounted on said proximal end of said inflation line defining a fluid inlet for connecting said proximal end of said inflation line to a source of liquid to supply liquid to the interior of said cuff, and a plug manually insertable into said fluid inlet to seal said fluid inlet.

4. An assembly according to claim 3, wherein the major portion of said inflation line between its proximal and distal ends extends along said flexible metal conduit and is encased within said sheath.

5. An assembly according to claim 4, wherein said flexible metal conduit comprises a plurality of ring segments with adjacent segments flexibly joined together.

6. An assembly according to claim 4, wherein said tube includes indexing means aligned with said inflation line for indicating the location of said inflation line.

7. An assembly according to claim 1, wherein said flexible metal conduit is made of aluminum.

8. An assembly according to claim 1, wherein said fluid inlet of said inflation line is adapted for communication with a source of saline solution.

9. A tracheal tube assembly for use in intubation of a patient during laser surgery, comprising:

an elongated flexible metal conduit having a first end and a second end, a silicone sheath having a first end, a second end, and an outer surface, said elongated conduit being enclosed within said silicone sheath with said first end of said sheath disposed adjacent to said first end of conduit and said second end of said sheath enclosing said second end of said conduit, a cuff on said sheath enclosed elongated metal conduit adjacent to the first end of the conduit, said cuff including a resilient body portion and a flexible tubular cover disposed on said body portion in surrounding relation thereto, and said cover having first and second ends secured to said outer surface of said sheath, and fluid coupling means for communicating the interior of said cuff with a source of a vacuum for collapsing said cuff to a collapsed condition to facilitate insertion of the tube assembly into the patient's trachea, and thereafter communicating the interior of said cuff with a source of liquid to receive liquid from the source of liquid to fill said cuff with liquid from the source of liquid to saturate said body portion of said cuff with the liquid and to expand said cuff from the collapsed condition to an expanded condition into engagement with the inner wall of the trachea of the patient to form a seal between said cuff of the tube assembly and the inner tracheal wall of the patient, the liquid saturated body portion of said cuff defining a heat dispersion medium for absorbing laser energy impinging on said cuff and maintaining a seal between said cuff and the inner wall of the trachea of the patient in the event the cover is penetrated by the laser beam.

10. A tracheal tube assembly according to claim 9, wherein said fluid coupling means comprises an inflation line having a proximal end and a distal end, said distal end of said inflation line extending into said cuff in fluid communication with the interior thereof, and connector means mounted on said proximal end of said inflation line defining a fluid inlet for connecting said proximal end of said inflation line to the source of vacuum and to the source of liquid.

11. A tracheal tube assembly according to claim 10, wherein said connector means comprises a connector body defining said fluid inlet, and a plug manually insertable into said fluid inlet to seal said fluid inlet.

* * * * *